US010451459B2

(12) United States Patent
Copley et al.

(10) Patent No.: US 10,451,459 B2
(45) Date of Patent: Oct. 22, 2019

(54) APPARATUS FOR INHALER TESTING

(71) Applicant: Copley Scientific Limited, Nottingham (GB)

(72) Inventors: Mark Andrew Copley, Nottingham (GB); Benjamin Bradley, Nottingham (GB); Ian Christopher Evans, Nottingham (GB); Jonathan Charles Stephen Wright, Nottingham (GB)

( * ) Notice: Subject to any disclaimer, the term of this patent is extended or adjusted under 35 U.S.C. 154(b) by 85 days.

(21) Appl. No.: 15/874,952

(22) Filed: Jan. 19, 2018

(65) Prior Publication Data

US 2018/0259379 A1 Sep. 13, 2018

(30) Foreign Application Priority Data

Mar. 13, 2017 (GB) .................................. 1703990.0

(51) Int. Cl.
| | | |
|---|---|---|
| *A61M 15/00* | (2006.01) | |
| *A24F 15/06* | (2006.01) | |
| *G01F 1/36* | (2006.01) | |
| *A61M 16/14* | (2006.01) | |
| *G01M 1/00* | (2006.01) | |
| *A61M 16/00* | (2006.01) | |

(52) U.S. Cl.
CPC .............. *G01F 1/36* (2013.01); *A61M 15/00* (2013.01); *A61M 16/026* (2017.08); *A61M 16/14* (2013.01); *G01M 1/00* (2013.01); *A61M 2016/0027* (2013.01); *A61M 2016/0039* (2013.01); *A61M 2202/064* (2013.01); *A61M 2205/70* (2013.01)

(58) Field of Classification Search
CPC .............................. A61M 15/00; A61M 15/06
See application file for complete search history.

(56) References Cited

U.S. PATENT DOCUMENTS

| | | | |
|---|---|---|---|
| 5,622,164 A | 4/1997 | Kilis et al. | |
| 5,655,520 A * | 8/1997 | Howe ............... | A61M 15/0086 128/203.12 |
| 7,604,006 B2 | 10/2009 | Wolf et al. | |
| 7,659,725 B2 | 2/2010 | Mueting et al. | |
| (Continued) | | | |

FOREIGN PATENT DOCUMENTS

| | | |
|---|---|---|
| WO | 2004112702 | 12/2004 |
| WO | 2014033439 | 3/2014 |

OTHER PUBLICATIONS

Great Britain Patent Application No. GB1703990.0 Search Report dated Jul. 21, 2017.

*Primary Examiner* — Jewel V Dowtin
(74) *Attorney, Agent, or Firm* — Leber IP Law; Celia H. Leber

(57) ABSTRACT

There is disclosed inhaler testing apparatus, in which at least one flow regulation valve, such as a needle valve, is located within a conduit. The flow regulation valve divides the conduit into inlet and outlet sides of the valve. The inlet side is arranged for connection to an inhaler and the outlet side for connection to a vacuum source. An electric motor provides variable adjustment of a flow opening through the valve. At least one sensor senses pressure or flow rate in the inlet side and a controller automatically adjusts the flow opening through the valve in response to readings from the at least one sensor. The apparatus may also comprise a shut off valve, such as a solenoid valve.

25 Claims, 2 Drawing Sheets

(56) References Cited

U.S. PATENT DOCUMENTS

| | | |
|---|---|---|
| 8,336,397 B2 | 12/2012 | Lehmann |
| 8,538,707 B2 | 9/2013 | Adamo et al. |
| 9,599,550 B2 | 3/2017 | Van Der Mark et al. |
| 9,993,602 B2 * | 6/2018 | Davidson ............... A61K 9/007 |
| 2004/0261792 A1 | 12/2004 | Wolf et al. |
| 2016/0302484 A1 | 10/2016 | Gupta et al. |

* cited by examiner

APPARATUS FOR INHALER TESTING

BACKGROUND

The present invention relates to apparatus for inhaler testing, and in particular to apparatus for dry powder inhaler (DPI) testing.

The vast majority of Dry Powder Inhalers (DPIs) are classified as "passive" breath actuated devices; that is to say, they rely solely on the patient's inspiration to operate. There is no necessity to co-ordinate breathing with the actuation—the patient simply inhales deeply to access the drug. It follows that both the delivered and fine particle dose of DPIs are dependent on the strength and duration of the patient's inspiration, a critical quality attribute (CQA) which must be simulated during the course of in vitro testing. The testing of DPIs is further complicated by the fact that different inhalers provide varying degrees of resistance to flow i.e. some require more effort to inhale than others.

In the case of the in vitro testing of DPIs, the European and US pharmacopoeias specify that the duration of a single inhalation cycle (equivalent to that of a typical user when inhaling the drug) be achieved through the use of a 2-way switching valve connected to a vacuum pump. The operation of the switching valve, and hence the duration of the breathing cycle, is controlled by means of a timer. One side of the valve is connected to either the sampling apparatus (in the case of delivered dose) or a cascade impactor (in the case of particle size determination) and the other to a vacuum pump. In pre-test mode, the switching valve is in the closed position such that no flow passes through the test apparatus. On initiation of the test, the 2-way valve switches such that flow now passes through the test apparatus and hence the inhaler under test. On expiration of the pre-set time, the solenoid closes again and the "inhalation" cycle is complete.

In the in vitro case, the in vivo strength and duration of the user's inspiration is replicated by the flow rate used and the time for which the solenoid valve concerned remains open. To establish the correct flow rate to be used, it is first necessary to establish the flow rate required to produce a pressure drop comparable with that found at the mouth of the user in vivo when using the particular inhaler being studied. Both European and US Pharmacopoeias suggest a pressure drop over the inhaler of 4 kPa as being broadly representative of the pressure drop generated during inhalation by adult patients using DPIs. The pressure drop created by the air drawn through an inhaler can be measured directly by measuring the absolute pressure downstream of the inhaler mouthpiece and comparing this directly with atmospheric pressure.

It is known to use a flow control valve to manually adjust the flow rate from the vacuum pump to produce the required pressure drop of 4 kPa and then, by replacing the inhaler with a suitable flow meter, to measure the flow rate, Q, required to produce this pressure drop. It is this flow rate, Q, that the Pharmacopoeias state should be used for the determination of both delivered dose uniformity and aerodynamic particle size distribution. The only exception to this criterion is that if the flow required to produce a 4 kPa pressure drop is >100 L/min, as for example in the case of particularly low resistance inhalers, whereupon 100 L/min should be used.

An example of existing apparatus used to perform this testing is the Copley Critical Flow Controller Series TPK available from Copley Scientific. Whilst existing products which perform the aforementioned testing more than adequately perform their function, the requirement to manually adjust a flow control valve is prone to inaccuracies caused by manual adjustment of the valve, and hence can be time consuming.

SUMMARY

There has now been devised apparatus for inhaler testing which overcomes or substantially mitigates the aforementioned and/or other disadvantages associated with the prior art.

According to a first aspect of the present invention there is provided inhaler testing apparatus comprising a conduit having at least one flow regulation valve located within the conduit and dividing the conduit into inlet and outlet sides of the valve, the inlet side being arranged for connection to an inhaler and the outlet side for connection to a vacuum source, an electric motor for variable adjustment of a flow opening through the valve at least one sensor for sensing pressure or flow rate in the inlet side, and a controller for automatically adjusting the flow opening through the valve in response to readings from the at least one sensor.

The inhaler testing apparatus according to the first aspect of the present invention may be advantageous principally as the apparatus comprises a controller for automatically controlling operation of the valve in response to pressure sensed by the at least one pressure sensor. In particular, this may remove the need for the user to manually adjust the valve to achieve a desired pressure differential across an inhaler to be tested.

The inhaler testing apparatus may comprise a device for dosimetry testing, for example dosimetry testing of inhalers. The inhaler testing apparatus may comprise a device for testing dry powder inhalers (DPIs). The inhaler testing apparatus may comprise a device for dosimetry testing of dry powder inhalers. The inhaler testing apparatus may comprise a device for testing uniformity of delivered dose (DDU) of inhalers, for example dry powder inhalers. The inhaler testing apparatus may comprise a device for testing dose content uniformity (DCU) of inhalers, for example dry powder inhalers.

The valve may comprise a needle valve, for example a valve comprising a valve seat and a needle-like valve member selectively engageable with the valve seat.

The valve may comprise a multi-turn valve. The valve may comprise a valve seat and a profiled or needle-like valve member which is rotatable to selectively position the valve member relative to the valve seat. The valve member may comprise a threaded portion for axial actuation by rotation of the threaded portion.

The valve may comprise a valve having a flow co-efficient of one or more.

The first end may be in fluid communication with an inhaler in use, for example in a pressure-differential setting mode or configuration. The first end may be connected to an inhaler in use, and may, for example, be indirectly connected to an inhaler with an intermediate component therebetween. The intermediate component may comprise a particle collection device.

The at least one pressure sensor may be in fluid communication with a mouthpiece of an inhaler and/or ambient pressure, for example ambient external pressure, in use. The controller may be configured to automatically control operation/adjustment of the valve in response to a pressure sensed in the particle collection device, for example a pressure sensed at or just outside a mouthpiece of the inhaler. The controller may be configured to automatically control operation of the valve in response to a pressure differential sensed between the interior of the particle collection device and ambient external pressure, for example a pressure differential sensed between an outlet of the mouthpiece of the inhaler and ambient external pressure.

The at least one pressure sensor may comprise a differential pressure sensor, for example a differential pressure sensor having first and second ports. The differential pressure sensor may be configured to have at least one port in fluid communication with the interior of the particle collection device, and at least one port in fluid communication with ambient atmosphere. The controller may be configured to automatically control operation of the valve in response to a pressure differential sensed by the differential pressure sensor.

The controller may be configured to control operation, for example movement, of a valve member of the valve in response to pressure sensed by the at least one pressure sensor. The controller may be configured to control operation of the valve to achieve a desired and/or predetermined pressure differential/drop across the inhaler. The controller may be configured to achieve a pressure drop of 4 kPa across the inhaler. The device/controller may thus be able to accommodate a range of different inhalers by automatically adjusting to achieve a pre-set pressure drop for the particular inhaler that is currently connected.

The controller may be configured to control opening and/or closing of the valve member in response to pressure sensed by the at least one pressure sensor. The controller may be configured to control the position of a valve member of the valve relative to a valve seat of the valve, in response to pressure sensed by the at least one pressure sensor. The controller may be configured to cease automatic control of the valve once a desired pressure differential, for example a pressure drop of 4 kPa, across the inhaler has been achieved.

The valve may be variably adjustable between fully open and closed conditions. The actuator may adjust the valve to vary the area and/or profile of a flow opening through the valve.

The actuator may be connected to the valve member of the valve.

The actuator may be indirectly connected to the valve, for example by an intermediate coupling. The actuator may comprise a rotor and/or the coupling.

The intermediate coupling may be configured to allow for relative movement, for example relative axial movement, between the actuator and the valve, in use. The intermediate coupling may comprise first and second coupling members which are movably coupled to one another. The first and second coupling members may be axially movably coupled to one another, e.g. along an axis of rotation of the actuator and/or coupling. The first and second body portions may be slidably coupled to one another. The intermediate coupling member may thus eliminate the need for the actuator to move axially, which, for example, is typically required when utilising a screwing motion to maintain contact between the actuator and the object to be screwed.

The actuator may comprise a motor for causing movement/rotation of a valve member of the valve. The actuator may drive axial movement of a valve member of the valve, for example movement of the valve member in a direction along its longitudinal axis or axis of rotation. The actuator may comprise a motor for screwing and/or unscrewing a valve member of a needle valve relative to the valve seat.

The motor may, for example, comprise a stepper motor. In presently preferred embodiments the motor comprises a motor which allows a continuous range of movement, which may, for example, allow for finer control of the position of the valve member relative to the valve seat, and hence finer control over the pressure drop across the inhaler.

The controller may comprise at least one processor configured to receive readings from the at least one pressure sensor, e.g. for automatic control of operation of the actuator in response to said readings.

The actuator may be configured to provide feedback to the controller. The controller may be configured to automatically control operation/movement of the valve in response to feedback received from the actuator. The controller may be configured to cease operation of the actuator in response to feedback received from the actuator.

The controller may be arranged to de-energise the motor, upon determination of a predetermined/desired condition, e.g. a pressure or pressure differential/drop. The valve position may thus be held in a position corresponding to said predetermined condition by friction or a mechanical lock.

The controller may operate according to an iterative routine, e.g. to converge on a valve position corresponding to the predetermined/desired condition. The controller may estimate and implement a valve position change based on a current and/or previous pressure reading. The degree/magnitude of valve displacement at each iterative step may be based upon the change in condition caused by a previous step, e.g. relative to the desired condition.

A proportional-integral-derivative (PID) controller or control scheme may be used.

The actuator may comprise any or any combination of: a torque sensor for sensing torque applied to a valve member; a current sensor for sensing current drawn by the actuator in use; and/or a position sensor for sensing the position of the driving member in use. The driving member may be configured to provide feedback to the controller based on the sensor reading of any or any combination of said sensors. The controller may be configured to cease operation of the actuator/valve in response to said feedback, for example where a measured/sensed value exceeds a pre-determined threshold value. The controller may prevent over-tightening of the valve member past a fully open and/or fully closed configuration, and may prevent jamming of the valve in use.

The position sensor may comprise a displacement transducer, for example a potentiometer. The controller may be configured to cease operation of the actuator/valve, when a measured valve and/or actuator position deviates from a pre-determined position value.

The controller may be configured to perform automatic calibration of the valve. For example, the controller may be configured to automatically determine a fully open and/or fully closed configuration of the valve. The controller may perform a calibration routine upon start-up, e.g. upon commencement of an instance of use or prior to normal use of the device for inhaler testing.

The controller may be configured to perform automatic calibration of the valve, e.g. determining fully open and/or fully closed valve conditions, in response to sensor readings provided by any or any combination of the sensors referred to herein, e.g. pressure, torque, current and/or position sensor(s). The controller may be configured to automatically determine a fully open/closed configuration of the valve in response to a plurality of position readings sensed by the at least one position sensor.

A rotary encoder, e.g. an absolute encoder or angle transducer, may be used for the motor. The controller may set one or more operational limit (e.g. an index point) of the encoder according to a sensed or predetermined fully closed and/or fully open valve configuration, which may for example be determined during calibration.

The controller may be configured to automatically determine a fully open configuration of the valve in response to a measurement made by a position sensor, for example a position sensor disposed on the actuator/coupling.

An inhaler may be connected to the first end and/or a vacuum source may be connected to the second end. An inhaler may be connected to the first end indirectly, e.g. via a dosage uniformity sampling apparatus (DUSA) and/or an impactor.

The inhaler testing apparatus may comprise a vacuum source connected to the second end.

The inhaler testing apparatus may comprise a user interface for input of desired parameters to the device/controller. The inhaler testing apparatus may comprise a user interface for setting a desired pressure differential/drop across the inhaler. The user interface may comprise a plurality of buttons which allow data to be input, which may, for example, comprise touchscreen buttons.

The inhaler testing apparatus may comprise a further valve located in the conduit, for example at a location spaced from the flow regulation valve, such as towards the second end of the conduit. The further valve may allow for selective fluid communication between the vacuum source and the conduit. The further valve may comprise an on/off or shut off valve, e.g. as distinct from a flow regulation valve. The further valve may comprise a solenoid valve. The further valve may be automatically controlled by the controller and/or a further control circuit.

The inhaler testing apparatus may comprise at least one flow sensor for sensing fluid flow across the valve, for example fluid flow between the inlet portion and outlet portion. The controller may automatically control operation of the valve (e.g. the valve member and/or actuator) in response to fluid flow sensed by the at least one flow sensor, for example in a flow-setting mode or configuration. The controller may be configured to control operation of the valve to achieve a desired flow rate across the valve, for example a desired flow rate between the first and second ends. The controller may control the position of a valve member of the valve relative to a valve seat of the valve, in response to fluid flow sensed by the at least one flow sensor. The first end may be connected to a particle impactor, e.g. a cascade impactor, or a flow sensor, in the flow-setting mode or configuration.

The inhaler testing apparatus may comprise first and second pressure sensors for sensing a pressure either side of the valve, for example first and second absolute pressure sensors. The controller may automatically control operation of the valve in response to absolute pressures sensed by the first and/or second pressure sensors, for example in a valve pressure differential setting mode or configuration. The controller may be configured to control operation of the valve to achieve a desired ratio of pressures sensed either side of the valve, for example a pressure ratio less than or equal to 0.5.

The inhaler testing apparatus may be operable to achieve at least one, and in preferred embodiments all, of the following: to automatically control operation of the valve to achieve a desired pressure drop across an inhaler; to automatically control operation of the valve to achieve a desired flow rate through the conduit; or to automatically control operation of the valve to achieve a desired ratio of pressures either side of the valve.

According to further aspects of the invention, there may be provided a method of controlling inhaler testing apparatus and/or an inhaler test apparatus controller corresponding to the first aspect.

It will be recognised that optional features described above in relation to the first aspect of the present invention may be equally applied to other aspects of the present invention, where appropriate.

Practicable embodiments of the invention is described in further detail below with reference to the accompanying drawings, of which:

DETAILED DESCRIPTION

Figure 1:
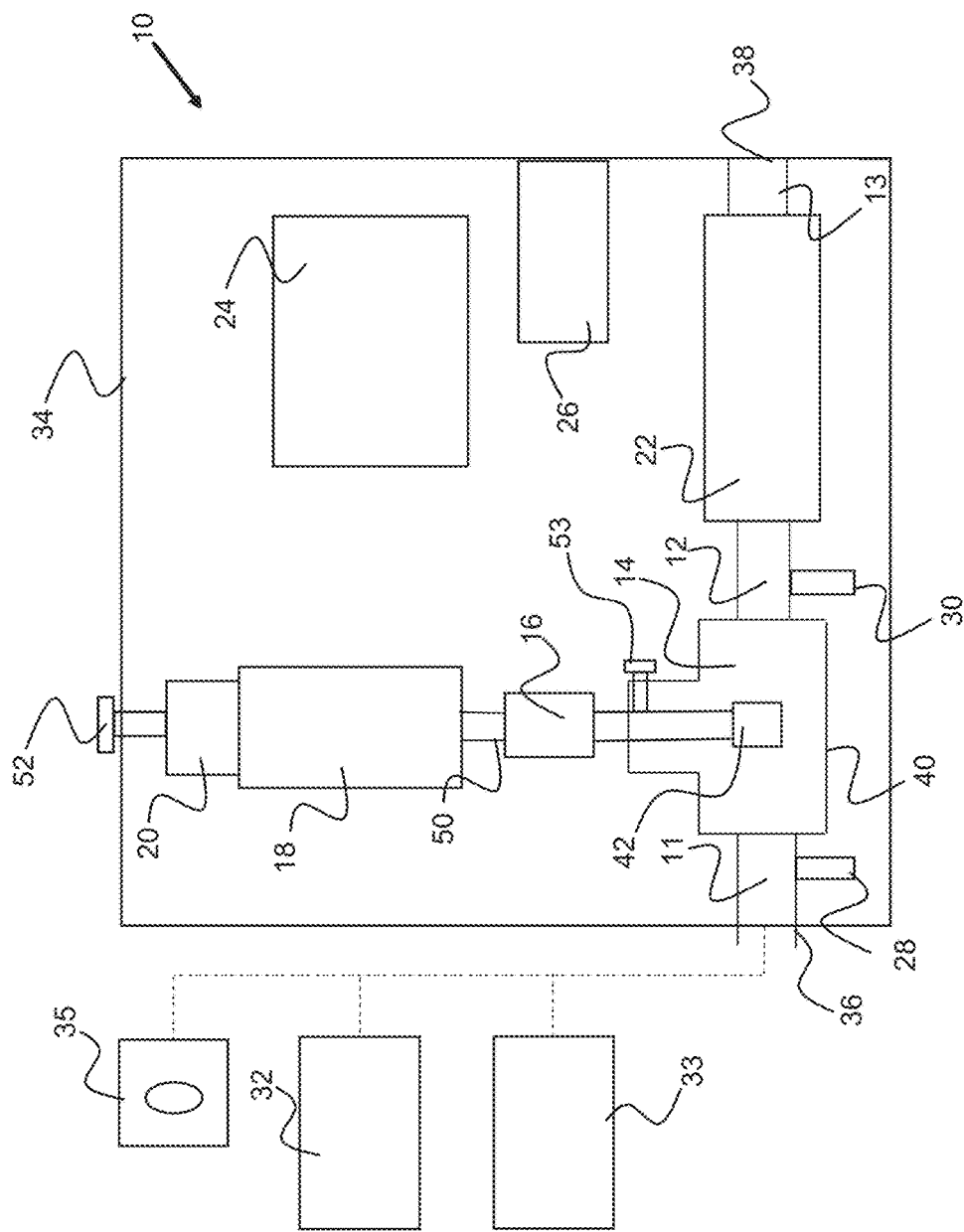
FIG. 1 is a schematic view of apparatus for inhaler testing according to the first aspect of the present invention.

A device for inhaler testing according to the present invention, generally designated 10, is shown schematically in FIG. 1.

The device 10 comprises first 11, second 12, and third 13 conduit portions, a needle valve 14, a coupling member 16, a drive motor 18, a position sensor 20, a two-way solenoid valve 22, a control circuit 24, a differential pressure sensor 26, first 28 and second 30 absolute pressure sensors, and a flowmeter 32. In this exemplary embodiment, each component of the apparatus 10 is housed in a common housing 34, other than the flowmeter 32.

A first end of the first conduit portion 11 defines an inlet 36 for the device 10, such that inhaler testing apparatus, for example a particle collection device 33 and/or an impactor and/or the flowmeter 32 can be connected to the inlet 36, in use, either directly or indirectly via intermediate components. The inlet 36 may comprise a connector for connection of a further conduit leading to a connector for attachment of any or any combination of the flow meter 32, the particle collector 33 and/or an impactor in use. The inhaler connector 35 has an opening for receiving an inhaler to be tested in use. The particle collector 33 and inhaler connector 35 may be connected in flow series in use such that particulate material flows from the inhaler connector 35 to the particle collector 33. Thus the particle collector is downstream of the inhaler collector in the direction of flow towards the inlet 36, when connected.

The particle collection device may comprise a chamber having a filter material, or other particle collecting material, arranged in the flow path between the inhaler and device 10. In some examples, the particle collecting material may be insertable/attachable to the inhaler connector. The particle collection/analysis device 33 could additionally or alternatively comprise an impactor, e.g. used to collect particle samples in a fractionated manner as an indication of particle size distribution within the flow. Such an impactor device would typically be separate from the inhaler connector 35 and connected thereto by a further conduit portion.

The flow meter 32 may be selectively connectable to the first conduit portion 11 instead of the inhaler connector 35 and/or particle collector 33.

A second end of the first conduit portion 11 is connected to an inlet of the main body 40 of the needle valve 14. Thus the external components, e.g. the flow meter 32, particle collector 33 and/or inhaler connector 35 can be connected in flow communication with the needle valve 14 for use.

A first end of the second conduit portion 12 is connected to an outlet of the main body 40 of the needle valve 14, whilst a second end of the second conduit portion is connected to an inlet of the two-way solenoid valve 22. A first end of the third conduit portion 13 is connected to an outlet of the two-way solenoid valve 22, whilst a second end of the third conduit portion 13 defines an outlet 38 for the apparatus 10. Collectively, the first 11, second 12, and third 13 conduit portions, along with the needle valve 14 and the two-way solenoid valve 22 define a flow path from the inlet 36 to the outlet 38 of the device 10.

The needle valve 14 comprises a main body 40 which houses a valve seat (not shown) and a rotatable valve member 42. The valve seat and member are typically correspondingly contoured so as to allow control of the available flow area/volume through the valve by adjustment of the valve member towards and away from the valve seat. The controlled adjustment of the position of the valve member 42 relative to the valve seat allows regulation of the flow through the valve body 40, e.g. to achieve a desired flow rate or pressure drop through the valve.

The needle valve has a flow coefficient, $C_v>1$, and requires multiple turns to be actuated between fully open and fully closed conditions, e.g. to allow accurate flow control. The valve member 42 and corresponding portion of the main body 40 may thus comprise threaded formations to control the axial position of the valve member 42 relative to the valve seat according to the rotation of the valve member.

The valve member has a stem or shaft for connection to the motor 18 via coupling 16.

Figure 2:
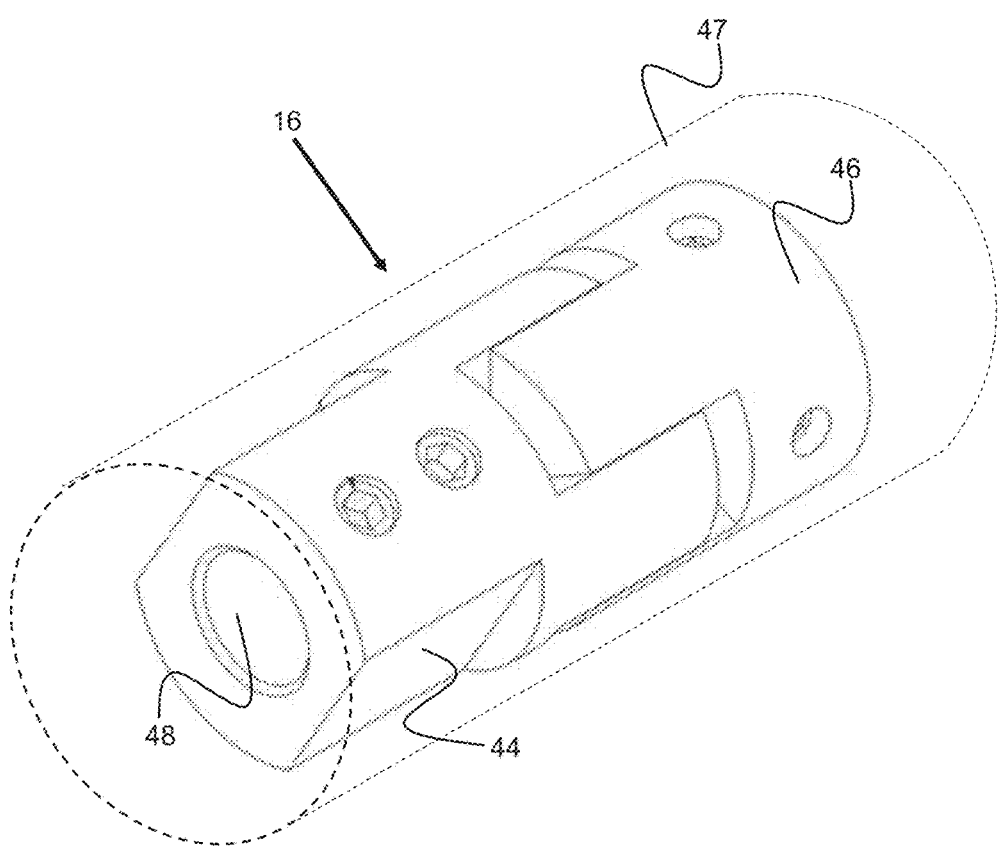
FIG. 2 is a schematic perspective view of a coupling member for use with the apparatus of FIG. 1.

The coupling member 16 is shown schematically in FIG. 2. The coupling member 16 comprises first 44 and second 46 opposing body portions which are slidably mounted relative to one another. Either or both body portion 44/46 has one or more projection which is slidably received in an opposing recess/slot in the other body portion. The projection and opposing recess both extend in a direction of the axis of rotation of the coupling member 16 in use and allow torque transfer there-between. Thus the first and second body members can move towards or away from each other up to a maximum spacing defined by the length of the projection/recess, before becoming disengaged.

In this example the projections and slots are general trapezoidal or wedge-shaped in section. Three projections are provided on each body portion which interfere with opposing, angularly offset projections on the opposing body portion. Thus the opposing ends of the body portions are castellated in form. However other slidable interference-fitting formations may be provided in other embodiments.

The corresponding projections and slots have one or more radially extending face for torque transfer there-between. In this example, the opposing, radially-extending faces of the projections each provide force transfer faces for torque transfer in forward and reverse directions. Thus a close, but slidable, engagement between adjacent projections is desirable in this example so that a direct coupling is achieved in either direction. The relative angular orientation of the opposing faces (e.g. due to the wedge-shape of each projection) may allow a suitable tolerance for the desired close fitment.

The first body portion 44 has a formation 48 shaped and dimensioned to receive a drive member 50 of the drive motor 18, whilst the second body portion 46 has a formation (not shown) shaped and dimensioned to receive the rotatable valve member 42 of the needle valve 14.

The coupling member 16 is shown as being housed within an optional jacket or housing 47 in this example. The jacket 47 is shown in phantom and may comprise a generally tubular body which may serve to align/constrain the coupling members in use, e.g. to maintain axial alignment thereof whilst permitting rotational and axial movement in use.

The drive motor 18 serves as the actuator for the valve member 42, e.g. along with the coupling 16. The drive motor is an electric motor allowing electric current to drive rotation of a rotor 50, such as a shaft/axle, in opposing rotational directions. The rotor 50 acts as a drive member for applying torque to the valve member 42 via the coupling 16. Any conventional electric motor capable of tightly controlled angular adjustment may be used, e.g. such as a stepper motor. However in this example, a DC permanent magnet brushed geared motor is used. An electric motor which can selectively hold an energised but static state of the output rotor 50 has been found to be advantageous.

The position sensor 20 in presently preferred embodiments is a multi-turn potentiometer. The position sensor 20 is mounted to the drive motor 18 in this example and determines the position of the valve member 42 according to the angular movement/position of the rotor 50. In other examples, a position sensor could be mounted on the valve 14, e.g. to determine the relative spacing between the valve member and valve seat. Additionally or alternatively, a position sensor could be mounted on the coupling 16, e.g. to determine a relative axial spacing of the opposing coupling members to determine the position of the valve member. Accordingly, various examples of alternative/equivalent sensor could be used to determine the axial position of the valve member 42 for flow control.

The two-way solenoid valve 22 is a conventional solenoid valve, with an example of an appropriate solenoid valve being Co-ax valves Mk10 2/2 direct acting solenoid valve. However, aspects of the invention may reside in the combined/automated use of a solenoid/shut-off valve with the flow regulation valve 14. The valve 22 is required to be opened in this example to allow iterative adjustment and/or normal use of the flow regulation valve 14.

The two-way solenoid valve 22 is located between the needle valve 14 and the outlet 38 of the apparatus 10. Unlike the flow regulation of the needle valve 14, the solenoid valve serves as a shut-off valve to selectively expose or isolate one side of the valve from fluid pressure on the other.

The control circuit 24 has at least one processor which is configured to control operation of the drive motor 18, and is configured to receive feedback from any one or more of the position sensor 20, the differential pressure sensor 26, the first 28 and second 30 absolute pressure sensors, and a user interface of the apparatus 10 (not shown). The processor of the control circuit may comprise one or more programmable processor operating under machine readable instructions in the form of executable code so as to process the relevant sensor/data inputs and generate control instructions for operating the valve 14 and any other associated components of the apparatus as described herein.

The differential pressure sensor 26 is configured to sense a pressure differential across an inhaler connected to the device 10 in use. The differential pressure sensor 26 has first and second ports, the first port being in fluid communication the interior of a particle collection device 33 or the inhaler connector 35 in use, and the second port being in fluid communication with ambient conditions. In other examples, the first port could potentially be exposed to the internal pressure in the system anywhere upstream of the flow regulation valve 14.

The first absolute pressure sensor 28 is located in the first conduit portion 11, between the inlet 36 and the needle valve 14. The second absolute pressure sensor 30 is located in the second conduit portion 12, between the needle valve 14 and the two-way solenoid valve 22.

The flowmeter 32 is separate to the remainder of the apparatus 10, and is selectively attachable to the inlet 36 of the apparatus 10, e.g. for a flow rate setting mode of operation. In other examples, the flow meter could be integrated with the remaining apparatus 34.

In use, the apparatus 10 can be used to automatically set a desired pressure differential and/or a desired flow rate, e.g. by the user simply entering the desired parameter value(s) on the user interface, such as a keypad.

Where it is desired to set a pressure differential, an inhaler (not shown) is connected to the connector 35 for fluid communication with the inlet 36, e.g. via a particle collection device 33, and a vacuum pump (not shown) is connected to the outlet 38. The differential pressure sensor 26 is arranged with one port in fluid communication with the interior of the inhaler connector 35, e.g. at a mouthpiece of the inhaler, and another port in fluid communication with ambient atmosphere.

A user inputs a desired pressure differential across the inhaler via the user interface of the apparatus 10. The vacuum pump is operated, and the two-way solenoid valve 22 is opened to allow fluid flow through the device 10 from inlet 36 to the outlet 38.

The differential pressure sensor 26 measures the pressure drop on the suction side of the inhaler, downstream of the inhaler mouthpiece within the flow circuit. The differential pressure sensor 26 provides feedback to the control circuit 24. Where the sensed pressure differential does not match the desired pressure differential inputted by a user, the control circuit 24 acts to operate the drive motor 18 to apply torque to the rotatable valve member 42, thereby controlling the opening of the needle valve 14 and altering the pressure drop at the inhaler mouthpiece.

When the desired pressure drop is achieved, operation of the drive motor 18 is ceased, and the needle valve 14 remains in the set position. Thus operation of the needle valve 14 may be automatically controlled to provide a desired pressure drop, eliminating the need for manual adjustment of the needle valve 14. In this example, the coils of the electric motor 18 are de-energised when the desired valve position is reached so that the friction in the system, e.g. between the valve member 42 and valve body 14 (and/or any friction inherent in the motor/coupling) is sufficient to hold the valve member in the desired position. In this regard it is noted that the friction has been found to provide a sustained fixed position over time. The de-energising of the motor is also preferred to avoid the potential creep that could occur if the motor is held at a static but energised state.

In this example, the further use of the motor could be inhibited until a change in the desired pressure drop is initiated by the user, or else if a change in valve position is detected by position sensor 20.

The drive motor comprises a rotary encoder, such that the available range of angular adjustment (i.e. rotation) of the motor is divided into multiple discrete increments, such as hundreds of steps, e.g. over a thousand increments in this example. The encoder may operate in conjunction with the position sensor 20. The controller can instruct the motor to turn to any of the discrete incremental positions within the available operational range. This in turn translates to a corresponding degree of adjustment of the valve member. The extremes of operation, i.e. the zero and maximum adjustment condition, thus define the limits of actuation of the motor and valve member.

The sliding coupling member 16 allows torque to be provided to, and corresponding rotation of, the valve member 42 by the driving member 50 without axial separation between the valve member 42 and the driving member 50 in use.

Where it is desired to set a flow rate, the flowmeter 32 is connected to the inlet 36, and connected to the control circuit 24, and a vacuum pump (not shown) is connected to the outlet 38. A user inputs a desired flow rate via the user interface of the apparatus 10. The vacuum pump is operated, and the two-way solenoid valve 22 is opened to allow fluid flow from the inlet 36 to the outlet 38. The flowmeter 32 reads the flow rate across the inhaler (for example the flow rate through the particle collection device 33 or a connected impactor) and provides feedback to the control circuit 24. Where the sensed flow rate does not match the flow rate inputted by the user, the control circuit 24 acts to operate the drive motor 18 to apply torque to the rotatable valve member 42, thereby controlling the opening of the needle valve 14 and altering the flow rate across the inhaler. When the desired flow rate is achieved, operation of the drive motor 18 is ceased, and the needle valve 14 remains in the set position. Thus operation of the needle valve 14 may be automatically controlled to provide a desired flow rate, eliminating the need for manual adjustment of the needle valve 14.

In either the pressure or flow rate automatic modes of operation, it will be appreciated that the flow regime through the apparatus causes a dynamic/transient environment in which sensor readings can fluctuate, even for a period of time in which the valve 42 is not being adjusted. The dynamic nature of the flow means that automated control of the valve member 42 is not straightforward.

A bespoke, iterative control regime has been implemented in which a difference (i.e. error) between the current flow rate or pressure reading and the desired pressure reading is determined at each iteration and converted into an estimated valve position adjustment to achieve the desired reading. The position adjustment is implemented and the process repeated with the aim of converging towards an acceptable threshold of the exact desired setting.

Due to the dynamic nature of the flow, the control scheme may make use of any or any combination of the following when calculating the next adjustment of the valve member position: an instantaneous pressure/flow rate difference; a time averaged pressure/flow rate difference; an instantaneous rate of change of pressure/flow rate; a rate of change of pressure/flow rate over time. Each iterative step may assess the change in any or any combination of said parameters due to a previous change in valve position and may adjust the magnitude or direction of the next change according to the impact of the previous change on the sensed pressure/flow rate.

The controller may store a plurality of previous changes and the related sensor readings to attempt further iterations that lie within a converging trend.

It has been found that using a step error approach of this kind can lead to wildly varying time to converge on a valve setting that achieves the desired flow/pressure condition. Accordingly it is proposed to implement an algorithm for determining a next change in valve position according to a function of the valve/device resistance and the current and/or previous step error.

In the current example, a PID control scheme is used. In this example, and/or further examples of the invention, it is possible that other sensor readings, e.g. the pressure sensors 28 and 30 could be used as further inputs in the control scheme to check compliance and/or ensure convergence of the iterative process.

According to examples of the invention, it may be proposed to use the pressure drop across the valve as a control parameter for automatic control of the valve position. For example, it has been found that the choking of the flow through the flow regulation valve may be desirable to maintain stable flow conditions. Accordingly a suitable threshold ratio of absolute pressure on either side of the valve may be maintained. A pressure drop of 0.5, less than 0.5, or approximately 0.5 may be used, such as between 0.47 and 0.50, may be used as a control parameter/limit, e.g. as a minimum pressure ratio In addition to the automated valve adjustment using pressure or flow rate readings, the apparatus allows a manual-adjustment mode of operation. A manual adjuster 52, e.g. a knob or wheel, is provided which causes rotation of the valve member 42. The adjuster 52 is shown in this example as acting on the motor 18, e.g. via the rotary encoder on the exterior of the motor housing. The motor is energised during manual adjustment and thus provides electrical assistance during manual adjustment of the valve. This can also be used to enable a suitable gearing or other rotary encoding between the manual adjuster 52 and the motor such that a 1:1 ratio between manual turns of the adjuster 52 and the valve member 42 may or may not be used. This ability to overcome the mechanical resistance in the system as well as providing fine manual control of the valve can be particularly useful.

A ratio of 10:1, 20:1 or more may be used for the manual input mechanism. In this example a 25:1 ratio is implemented using a worm drive mechanism.

During the manual adjustment mode, the pressure and/or flow rate readings can be presented to the user via the user interface. Thus user uses the manual adjuster to adjust the valve position via the motor rather than via a direct mechanical link with the valve member. In this mode, the control circuit reads the position of the encoder/adjuster 52 and causes the motor to rotate by an amount that is proportional to the movement of the encoder. The pressure drop/flow rate is displayed to the user so that the user can manipulate the encoder/adjuster 52 to achieve the desired flow condition. When the user ceases operation of the manual adjuster 52 the motor can be de-energised to hold the set valve position for subsequent use of the equipment for inhaler testing.

FIG. 1 also shows a further optional manual over-ride adjuster 53. In one example, this could be used in a manner similar to adjuster 52 described above for manual setting of the valve. However the friction inherent in the system has been found to detract from such a mode of general use without additional lever tools. Thus in the present example, it is proposed that the additional manual actuator provides a manual override available for use to free the system in the event of a valve jam or similar event in which the motor is unable to actuate the valve member 42 in the desired manner. The adjuster 53 may be connected between the motor and valve member 42, i.e. either side of the coupling 16 as desired. In one example, the adjuster 53 could take the form of a simple shaft portion, or shaft extension, to which a lever tool could be applied in use.

In any of the manual or automated modes of operation, the position of the valve can be logged in a memory. Thus the system could allow one or more pre-set valve positions to be recalled if necessary for future implementation. This could be particularly if a user is switching between inhaler types for testing but wishes to return to a previous inhaler setting at a later time.

The apparatus described herein is useful in allowing multiple modes of operation as follows:
  Automatic adjustment for pressure (P1 across inhaler)
  Automatic adjustment for flow rate
  Automatic adjustment for pressure drop across the flow regulation valve
  Flow leak testing (i.e. applying a pressure drop and closing the inlet to monitor pressure loss over time)
  Manual adjustment for pressure drop or flow rate The apparatus 10 according to some embodiments can be controlled based on factory set limits and control increments for the motor. In other examples, the device 10 can be operated to calibrate the fully closed and/or fully open configuration of the needle valve 14. This may prevent over-closing and/or over-opening of the needle valve 14, which may reduce the risk of the needle valve 14 jamming during use. This process may also be useful to account for wear of the valve over time such that the control system can reassess the relevant extreme valve positions throughout the operational life of the valve.

To calibrate the fully closed configuration of the needle valve 14 a vacuum pump (not shown) is connected to the outlet 38. The vacuum pump is operated, and the two-way solenoid valve 22 is opened to allow fluid flow between the inlet 36 and the outlet 38. The two-way solenoid valve 22 is then closed.

The pressure in the second conduit portion 12 is read for a first time by the second absolute pressure sensor 30, and is fed-back to the control circuit 24. A pre-determined period of time is allowed to lapse and the pressure in the second conduit portion 12 is read for a second time by the second absolute pressure sensor 30, and is fed-back to the control circuit 24. The first and second pressure readings are compared 104.

If the first and second pressure readings are within a pre-determined threshold percentage of one another, then the needle valve 14 can be determined to be in a fully closed position, and this position is logged by the control circuit 24, typically by recording the corresponding reading for the motor's rotary encoder. Additionally or alternatively, a reading of position sensor 20 of the type described above could be used to log the fully closed position of the valve member.

If the first and second pressure readings are not within the pre-determined threshold percentage of one another, then the control circuit 24 acts to operate the drive motor 18 to apply torque to the rotatable valve member 42, thereby attempting to move the needle valve 14 into a fully closed configuration. The steps are repeated until the first and second pressure readings are within a pre-determined threshold percentage of one another, the needle valve 14 is determined to be in a fully closed position 106, and this position is logged by the control circuit 24. In some examples, the control circuit may act to tighten the valve in the fully closed condition, i.e. to apply torque so as to turn the valve member slightly further even when already fully closed. A fraction of a turn of the motor/valve member may be added for this purpose.

Once the fully closed valve position has been found, the control circuit 24 may partially retract the valve member from the fully closed position, i.e. by reversing the motor rotation, and then reclose the valve member to test/check the fully closed condition. The fully closed condition may then be logged and implemented once it has been checked.

The control circuit may establish an index point for the rotary encoder corresponding to the fully closed condition which serves as an operational limit of the motor in use, e.g. until the apparatus is next calibrated.

To calibrate the fully open position of the needle valve 14, the above process is repeated only driving the motor in the opposite direction in order to find and log the open valve condition.

Recalibration of the valve 14 may be performed at predetermined intervals, such as at each instance of use, e.g. upon start-up, or after a predetermined measure of use, such as number of uses (e.g. number of valve closures) or a predetermined measure of time.

In different examples of the invention, the specific pressure sensing steps described above may be substituted with other suitable sensors or sensing steps. For example, instead of using time spaced readings of a single pressure sensor on one side of the valve, two pressure sensors on opposing sides of the valve could be used to determine a difference therebetween. Suitable threshold values of pressure difference/drop could be used to determine valve open/closed conditions. Additionally or alternatively, flow rate sensors could be used.

What is claimed is:

1. An inhaler testing apparatus, comprising:
   a conduit having at least one flow regulation valve located within the conduit and dividing the conduit into inlet and outlet sides of the valve, the inlet side being arranged for connection to an inhaler and the outlet side for connection to a vacuum source,
   an electric motor for variable adjustment of a flow opening through the valve;
   at least one sensor for sensing pressure or flow rate in the inlet side; and,
   a controller for automatically adjusting the flow opening through the valve in response to readings from the at least one sensor.

2. The apparatus as claimed in claim 1, wherein the valve comprises a needle valve.

3. The apparatus as claimed in claim 1, wherein the at least one sensor comprises a pressure sensor in fluid communication with the inlet side and/or the outlet side, and the controller is configured to adjust a dimension of the flow opening through the valve in response to a pressure sensed in the inlet and/or outlet portion.

4. The apparatus as claimed in claim 1, wherein the at least one sensor comprises a differential pressure sensor arranged to sense the pressure drop across an inhaler connected to the inlet side.

5. The apparatus as claimed in claim 1, wherein the at least one sensor comprises a first absolute pressure sensor in fluid communication with the inlet side, and/or a second absolute pressure sensor in fluid communication with the outlet side.

6. The apparatus as claimed in claim 5, wherein the controller is configured to automatically control adjustment of the flow area through the valve in response to pressure sensed by the first and/or second absolute pressure sensor.

7. The apparatus as claimed in claim 1, wherein the valve comprises a rotatable valve member, and the controller is configured to control rotation of the valve member relative to a fully open and/or fully closed valve member position to achieve a desired pressure drop or flow rate through an inhaler connected to the inlet side in response to readings from the at least one sensor.

8. The apparatus as claimed in claim 1, comprising an intermediate coupling in the force path between the motor and the valve, wherein the intermediate coupling member is configured to allow for axial relative movement between the motor and the valve, in use.

9. The apparatus as claimed in claim 8, wherein the intermediate coupling comprises first and second coupling members which are opposingly engaged for torque transfer there-between and slidably coupled to one another.

10. The apparatus as claimed in claim 1, wherein the motor comprises an encoder configured to provide motor position feedback to the controller, and the controller is configured to automatically control operation of the valve in response to feedback received from the encoder.

11. The apparatus according to claim 1, wherein the controller operates according to an iterative control scheme using feedback from the at least one sensor to incrementally adjust the flow regulation valve according to a difference between a desired pressure or flow rate and a sensed pressure or flow rate for a current and/or previous iteration of the control scheme.

12. The apparatus according to claim 1, wherein the controller is a PID controller.

13. The apparatus according to claim 1, wherein the controller controls adjustment of the flow regulation valve at least in part as a function of the flow resistance through the valve.

14. The apparatus as claimed in claim 1, wherein the motor comprises a valve condition sensor for sensing any, or any combination of position, electrical current or torque applied to the valve, the valve condition sensor configured to provide feedback to the controller, and the controller is configured to cease operation of the motor in response to the feedback.

15. The apparatus as claimed in any claim 1, wherein the controller is configured to perform automatic calibration of the valve by running a routine to determine a fully open and/or fully closed configuration of the valve.

16. The apparatus as claimed in claim 15, wherein the controller is configured to automatically determine a fully open and/or closed configuration of the valve in response to pressure sensed by at least one pressure sensor.

17. The apparatus as claimed in claim 1, wherein the apparatus comprises at least one flow sensor for sensing fluid flow on the inlet side, and the controller automatically controls operation of the motor to adjust the valve flow opening through the valve in response to fluid flow sensed by the at least one flow sensor.

18. The apparatus as claimed in claim 1, further comprising a shut off valve for the conduit, wherein the shut off valve is also under the control of the controller.

19. The apparatus as claimed in claim 1, comprising a user interface for inputting a desired pressure drop across an inhaler to be connected to the inlet side and the controller being arranged to automatically adjust the flow regulation valve to achieve said input pressure drop.

20. The apparatus as claimed in claim 1, comprising a manual actuator for manual setting of the position of the flow regulation valve.

21. The apparatus as claimed in claim 20, wherein the manual actuator is connected to the motor, so as to cause rotation of the flow regulation valve via the electric motor.

22. The apparatus as claimed in claim 1, further comprising a particle collector connectable on the inlet side between the flow regulation valve and an inhaler in use.

23. The apparatus as claimed in claim 1, offering each of the following modes of adjustment of the flow regulation valve:
   automatic adjustment according to pressure;

automatic adjustment according to flow rate; and
manual adjustment by a manual actuator.

24. A data carrier comprising machine readable instructions for the operation of one or more processors of an inhaler testing apparatus controller to:
  i. receive a desired pressure or flow rate condition for an inlet side of a flow regulation valve of a flow conduit of the inhaler testing apparatus
  ii. receive sensor readings from a pressure or flow rate sensor in the inlet side of the flow conduit whilst a vacuum is being applied to an outlet side of the flow conduit downstream of the flow regulation valve by a pump;
  iii. compare the desired condition with the received sensor readings, determine an adjustment to the flow regulation valve and implement the adjustment to the flow regulation valve by outputting control instructions to an electric motor drivingly connected to said flow regulation valve;
  iv. iteratively repeat said steps ii and iii in order to converge on the desired condition; and
  v. control cessation of the electric motor once the desired condition is achieved.

25. The data carrier according to claim 24, wherein the controller is further arranged to control operation of a shut off valve to selectively allow fluid communication between the vacuum source and the inlet side via the flow regulation valve.

* * * * *